United States Patent [19]

Tuller et al.

[11] Patent Number: 5,654,038

[45] Date of Patent: Aug. 5, 1997

[54] POLYOL ESTERS OF ETHER CARBOXYLIC ACIDS AND FIBER FINISHING METHODS

[75] Inventors: F. Norman Tuller, Simpsonville; Michael E. Allen, Greenville, both of S.C.

[73] Assignee: Henkel Corporation, Plymouth Meeting, Pa.

[21] Appl. No.: 705,441

[22] Filed: Aug. 29, 1996

Related U.S. Application Data

[62] Division of Ser. No. 297,282, Aug. 29, 1994, Pat. No. 5,576,470.

[51] Int. Cl.⁶ ............................................. B05D 5/00
[52] U.S. Cl. ........................ 427/384; 427/394; 442/148; 508/465; 508/497
[58] Field of Search .................................. 427/394, 384; 252/8.6, 8.9

[56] References Cited

U.S. PATENT DOCUMENTS

| | | | |
|---|---|---|---|
| 5,240,743 | 8/1993 | Tuller et al. | 427/384 |
| 5,314,718 | 5/1994 | Tuller et al. | 427/394 |
| 5,576,470 | 11/1996 | Tuller et al. | 560/154 |

*Primary Examiner*—Samuel Barts
*Attorney, Agent, or Firm*—Ernest G. Szoke; Wayne C. Jaeschke; Real J. Grandmaison

[57] ABSTRACT

A compound of the general formula (I)

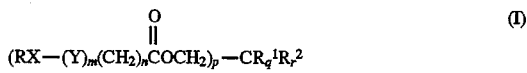

wherein R is alkyl from about 4 to about 22 carbon atoms, $R^1$ and $R^2$ independently of one another are alkyl from about 1 to about 22 carbon atoms, X is either sulphur or oxygen, Y is $-C_2H_4O-$ or $-C_3H_6O-$ or a mixture of $-C_2H_4O$ and $-C_3H_6O-$, m is a number from about 1 to about 20, n is a number from about 1 to about 6, p is a number from 2 to 4, q is a number from 0 to about 2 and r is a number from 0 to about 2, with q+r+p being the integer 4. This invention is also directed to the method for treating fibers by applying this compound.

11 Claims, No Drawings

POLYOL ESTERS OF ETHER CARBOXYLIC ACIDS AND FIBER FINISHING METHODS

This application is a divisional of Ser. No. 08/297,282 filed Aug. 29, 1994 now U.S. Pat. No. 5,576,470.

BACKGROUND OF THE INVENTION

1. Field of Invention

This invention relates to novel polyol esters of ether carboxylic acids. These polyol esters of ether carboxylic acids make good, high temperature stable, water-soluble/dispersible lubricants for fiber finishes.

2. Discussion of Related Art

Generally, in the case of many fiber materials, finishing compositions are applied to fibers to improve their subsequent handling and processing properties. Fiber finishes, in part, enable a fiber producer to manufacture a fiber product and in turn enable a purchaser of that product to utilize yarn and fabric manufacturing processes to obtain an end product. The composition and amount of a particular fiber finish applied depend in large measure upon the chemical characteristics of a particular fiber, the particular stage in the processing of the fiber at which it is applied, and the envisioned use of the particular fiber.

Such finishes generally provide lubrication, prevent static build-up, and afford a slight cohesion between adjacent fibers. Many other characteristics, however, are also desirable. For example, they should be easily applied to and removed from fibers and should be useful in subsequent treatment of the fibers. Also, they should have desirable thermal and chemical stability while not adversely affecting the fibers themselves. Such fiber finishes should not leave residues on objects they come in contact with nor cause toxic fumes or undesirable odors. They should provide for rapid wetting of fiber surfaces, be water-soluble or emulsifiable or solvent-soluble, and have good storage stability. Further, they should not attract soil, cause color changes to fibers, interact with frictional elements used in texturizing be corrosive to machine parts.

Application of such finishes may generally be accomplished by contacting a fiber tow or yarn with a solution, dispersion or emulsion comprising at least one lubricant having desirable antistatic properties. Additional antistatic agents, wetting agents, additives such as antioxidants, biocides, anti-corrosion agents, pH control agents, as well as emulsifiers are also commonly found in such finishes. A suitable fiber finish may also be sprayed or applied directly onto fibers or yarn.

In the past, fiber finishes were composed of many components in addition to a lubricant with each component imparting a desirable characteristic to the fiber finish. For example, in addition to the lubricant, antistatic agents were often added to increase the ability of the fiber to avoid buildup of static electric charge. Also, emulsifiers were often added to aid in the application to the fiber of the often oily and unmanageable lubricant.

Various lubricating agents have been disclosed by Ogiso et at. U.S. Pat. No. 4,615,816, Yamamoto et at. U.S. Pat. No. 4,505,956, Carver U.S. Pat. No. 3,951,825, Carver U.S. Pat. No. 3,907,689, Koleske U.S. Pat. No. 4,163,114, and Sturwold et at. U.S. Pat. No. 3,970,569. Various fiber finishes have been disclosed by Crossfield et at. U.S. Pat. No. 4,098,702 and Murase et at. U.S. Pat. No. 4,403,049. Casciani U.S. Pat. No. 4,766,153 discloses certain alkyl polyoxy alkylene carboxylates which are surface active agents and states that they are suitable as emulsifiers, dispersing agents, lubricants, wetting agents, levelling agents, and the like in the textile industry, e.g. as wetting, softening or lubricating agents. In addition, ether carboxylate esters have also been employed as plasticizers. See Bell et at. U.S. Pat. No. 2,803,646 and North U.S. Pat. No. 2,109,947.

A method for finishing fibers by applying a compound of the general formula

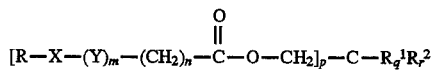

wherein $R_1$ is an alkyl from 1 to 23 carbon atoms, $R_2$ is a alkyl from 1 to 23 carbon atoms, n is a number from 3 to 15, and X is $-C_2H_4O-$ or $-C_3H_6O-$, or a mixture of $-C_2H_4O-$ and $-C_3H_6O-$ is disclosed and taught in U.S. Pat. No. 5,240,743, issued to Tuller et al.. However, Tuller et al. does not disclose nor teach a novel high temperature-stable ester having the general formula

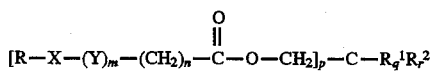

While these efforts may be satisfactory, they all involve the use of emulsifiers or have thermal stability problems and sometimes they are difficult to handle due to the viscosity of some compounds. Accordingly, a more desirable method is indicated which can impart desirable properties, e.g. lubricity, in fiber finishes. Such a method should have thermally stable lubricants which are able to be applied to a fiber with little or without the use of emulsifier:; while imparting desirable characteristics, e.g. lubricity.

BRIEF SUMMARY OF THE INVENTION

According to the present invention, novel compounds are provided of the general structure

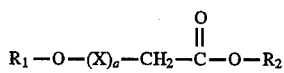

wherein R is an alkyl having from about 4 carbon atoms to about 22 carbon atoms, $R^1$ and $R^2$ independently of one another are an alkyl having from about 1 to about 22 carbon atoms, X is either a sulfur atom or an oxygen atom, Y is $-C_2H_4O-$ or $C_3H_6O-$ or a mixture of $-C_2H_4O-$ and $-C_3H_6O-$, m is a number from about 1 to about 20, n is an integer from 1 to 6, p is a number from 2 to 4, q is an number being from 0 to about 2 and r is a number being from 0 to about 2 with the sum of p+q+r being equal to 4.

According to the present invention, the desired fiber finishing, e.g. lubricity, is achieved by applying an effective amount of a compound selected from those having the general formula

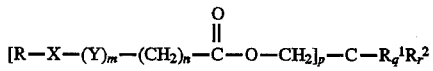

wherein R, $R^1$, $R^2$, X, Y, n, m, p, q and r are as defined above. An example of the effective amount of the compound would be about 0.01 to about 3 weight percent based on the weight of the fiber. These esters offer better thermal stability than the corresponding fatty add esters of ethoxylated polyols because they do not contain any hydrogen beta to the alcohol portion of the ester. The compounds useful in the present invention comprise a narrow class of ether carboxylic ester compounds that are thermally stable lubricants, which when applied to the fiber in the manner described below, exhibit desirable viscosity, lubricity, and ease of handling resulting in a diminished need to employ various other components and combinations therewith to be utilized in a fiber finish, thus minimizing the decrease in thermal stability resulting from other components. These and other features and advantages of the present invention may be more clearly understood by considering the following description of specific embodiments.

DESCRIPTION OF THE SPECIFIC EMBODIMENTS

According to the present invention, there is provided novel polyol esters of ether carboxylic acids of the formula (I)

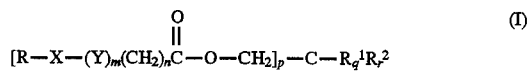

wherein R is a cyclic, straight, or branched chain alkyl, saturated or unsaturated, having from about 4 to about 22 carbon atoms. R may preferably have from about 8 to about 18 carbon atoms. X is sulphur or oxygen. The value for m may be a number from about 1 to about 20, preferably from about 4 to about 10, and more preferably from about 5 to about 8. The value of n may be a number from about 1 to about 6, preferably from about 1 to about 4. The value of p may be a number having the value from 2 to 4. $R^1$ and $R^2$ independently from one another, may be the same or different and may be cyclic, straight, or branched chain alkyl, saturated or unsaturated, having from about 1 to about 22 carbon atoms. $R^1$ and $R^2$ may preferably have about 1 to about 2 carbon atoms. As examples of alkyl, there may be mentioned methyl, ethyl propyl, butyl, pentyl, hexyl, septyl, octyl, nonyl, decyl, dodecyl, tetradecyl, hexadecyl, octadecyl, iso-octadecyl, stearyl, oleyl and the like. The values for q and r may be identical or different and may be a number 0 to 2. q+r+p is an integer with the value of 4. Examples of polyols which may be esterified with ether carboxylic acids to give the subject esters are neopentyl glycol, trimethylolethane, trimethylolpropane and pentaerythritol. These polyol esters of ether carboxylic acids make good, high temperature stable, water-soluble/dispersible lubricants for fiber finishes. These types of esters have better thermal stability than the corresponding fatty acid esters of ethoxylated polyols because they do not contain any hydrogen beta to the alcohol portion of the ester. This avoids the possibility of the classical cyclic elimination mechanism.

Also, according to the present invention, the desired fiber finishing, e.g. lubricity, is achieved by applying an effective lubricating amount of the compound selected from the general formula (I)

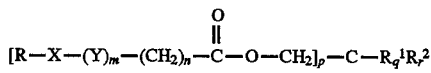

wherein R is a cyclic, straight, or branched chain alkyl, saturated or unsaturated, having from about 4 to about 22 carbon atoms. R may preferably have from about 8 to about 18 carbon atoms. X is sulphur or oxygen. Y is -$C_2H_4O$- or -$C_3H_6O$-, or a mixture of $C_2H_4O$- and -$C_3H_6O$-. The value for m may be a number from about 1 to about 20, preferably from about 4 to about 10, and more preferably from about 5 to about 8. The value of n may be a number from about 1 to about 6, preferably from about 1 to about 4. The value of p may be a number having the value from 2 to 4. $R^1$ and $R^2$ independently from one another, can be the same or different and may be cyclic, straight, or branched chain alkyl, saturated or unsaturated, having from about 1 to about 22 carbon atoms. The values for q and r may be identical or different and may be a number from 0 to about 2. q+r+p is an integer with the value of 4. An effective lubricating amount of the compound is from about 0.01 to about 3 percent, and preferably about 0.1 to about 1 weight percent, based on the weight of the fiber.

Compounds of formula I may be generally prepared by reacting an alcohol having a carbon chain of desired length, for example, any of the ranges previously mentioned, with an alkylene oxide such as ethylene oxide or propylene oxide, to form an alkoxylated alcohol. Synthesis may also begin with a previously synthesized alkoxylated alcohol. The alkoxylated alcohol is then reacted with a strong base, for example, a potassium or sodium base in the presence of a reducing agent such a sodium borohydride to form the corresponding potassium or sodium alkoxylate. This product is then reacted with sodium chloroacetate to form an ether carboxylic acid salt. This salt is then converted to the corresponding acid by washing with aqueous sulfuric acid. The ether carboxylic acid is then esterified by reaction with a desired polyol having a desired carbon structure, for example, any of the polyols previously mentioned to produce the compounds of the present invention.

In fiber finishing, these compounds may be applied alone or optionally by combining them with suitable antistatic agents and emulsifiers, if necessary, as well as other desirable fiber finish components. Fibers may be coated with an effective amount of the compounds of the present invention either alone or with other components of a fiber finish by towing a fiber strand through the compound or fiber finish or by directly spraying the compound or fiber finish onto the fiber. It should be understood that the compounds of the present invention exhibit suitable viscosity, lubricity and emulsifiability to enable their use alone or without certain of the above components in a fiber finish.

The following examples set forth certain specific embodiments of the invention and are provided to enable those of skill in the art to produce the compounds useful in the practice of the invention and to illustrate the utility of the invention in certain applications. These examples should not be construed to limit the scope of the invention, which is limited only by the lawful scope of the appended claims.

The fatty acid esters of polyols, such as pentaerythritol and trimethylolpropane, are widely used as heat-stable lubricants because they do not have hydrogen atoms beta to the ester linkages which can undergo cyclic elimination leading to thermal decomposition of the ester. However, these esters are very hydrophobic and must be used with emulsifiers when applied from an aqueous emulsion. These emulsifiers often are not thermally stable and detract greatly from the thermal properties of the system. Also, for fatty acids above a carbon chain of ten, these esters are often solids at ambient temperature which creates handling problems. One solution which has been used to overcome both of these problems is to ethoxylate the polyol before making the fatty acid ester. This tends to increase the hydrophilicity and decrease the melt point of the ester compared to the original ester. However, the introduction of the ethylene oxide chain into the molecule gives hydrogen atoms beta to the ester linkages which can then undergo cyclic elimination leading to thermal decomposition of the ethoxylated ester. This really compromises the original reason for using the polyol ester.

In this invention, polyol esters were made in which ether carboxylic acids have the ethylene oxide chains in the acid side of the ester rather than in the alcohol side as in the forementioned ethoxylated polyol esters. This approach allows the introduction of polyglycol chains into the molecule to assist in increased hydrophilicity and decreased melt point without having to sacrifice the absence of hydrogen atoms beta to the ester linkages to preserve the denial of the cyclic elimination route to thermal decomposition.

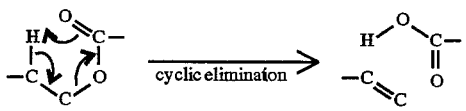

A series based on two widely used pentaerythritol esters have been selected. Pentaerythritol tetracaprylate is a low viscosity liquid at ambient temperature, while pentaerythritol tetralaurate is a solid. For each of these esters a one and a five mole ethylene oxide "EO" chain has been inserted on each side of the ester linkage. Also, for the ether carboxylic acid version of the five mole EO ester, a thiol linkage has been introduced to determine the effect of incorporating this internal antioxidant. This has created a grid of twelve samples with the following structures

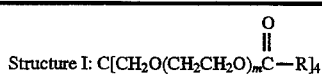

Structure I: $C[CH_2O(CH_2CH_2O)_mC-R]_4$

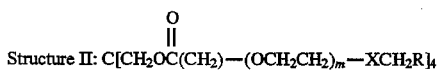

Structure II: $C[CH_2OC(CH_2)-(OCH_2CH_2)_m-XCH_2R]_4$

| Sample | Structure | m | R | X |
|---|---|---|---|---|
| Example I | I | 0 | $C_7H_{15}$ | — |
| Example II | I | 0 | $C_{11}H_{23}$ | — |
| Example III | I | 1 | $C_7H_{15}$ | — |
| Example IV | I | 1 | $C_{11}H_{23}$ | — |
| Example V | I | 5 | $C_7H_{15}$ | — |
| Example VI | I | 5 | $C_{11}H_{23}$ | — |
| Example VIIIa | II | 1 | $C_7H_{15}$ | O |
| Example VIIIb | II | 1 | $C_{11}H_{23}$ | O |
| Example VII | II | 5 | $C_7H_{15}$ | O |
| Example VIIIc | II | 5 | $C_{11}H_{23}$ | O |
| Example VIIId | II | 5 | $C_7H_{15}$ | S |
| Example VIIIe | II | 5 | $C_{11}H_{23}$ | S |

Structure I represents the ester of fatty acid reacted with ethoxylated pentaerythritol with m moles of EO. Structure II represents the ester of ether carboxylic acid containing m moles of EO reacted with pentaerythritol.

EXAMPLE I

PREPARATION OF PENTAERYTHRITOL TETRACAPRYLATE

To a flask for esterification having standard apparatus for agitation, heating and distillation was charged 1737 g (12 moles) of caprylic acid (alkyl chain 98% minimum C8, acid value 388 mg KOH/g). Agitation and a dry nitrogen sparge were started, and 363 g (2.7 moles) of pentaerythritol and 1.0 g of hypophosphorous acid solution (50%) were added. The contents were heated to 190° C. with the removal of the water of esterification by distillation and held at 190°–200° C. until all water was removed. The hydroxyl number of the contents was checked, and the reaction was continued at 190°–200° C. until a maximum hydroxyl number of 4.0 mg KOH/g was reached, indicating greater than 99% conversion to the ester. A vacuum was pulled via the distillation system to 30 inches and the contents were heated to 220° C. to remove the unreacted caprylic acid by distillation. The Acid value of the contents was checked, and the acid removal was continued at 220°–230° C. until a maximum acid value of 1.0 mg KOH/g was reached. The contents were then cooled to 70° C. and filtered to yield a compound of the formula $[C_7H_{15}COOCH_2]_4$-C

EXAMPLE II

PREPARATION OF PENTAERYTHRITOL TETRALAURATE

Following essentially the procedure for Example I, and using in place of the caprylic acid an equivalent amount of lauric acid (alkyl chain 98% minimum C12, acid value 279 mg KOH/g), a compound of the formula $[C_{11}H_{23}COOCH_2]_4$-C was obtained.

EXAMPLE III

PREPARATION OF POE(4) PENTAERYTHRITOL TETRACAPRYLATE a) Preparation of POE(4) Pentaerythritol To a flask for esterification having standard apparatus for agitation, heating and distillation was charged 2894 g (32.9 moles) of ethylene carbonate. Agitation and a dry nitrogen sweep were started, the contents were heated to 65° C., and 1106 g of pentaerythritol (8.1 moles) were added. The contents were heated to 105° C. and 8.0 g potassium hydroxide (82% minimum purity ground solid) was added. The contents were heated to 185° C. with removal of carbon dioxide and the hydroxyl number of the contents was checked. The reaction was continued at 185°–190° C. until a minimum hydroxyl number of 710 mg KOH/g was reached. The dry nitrogen sweep was changed to a sparge, a vacuum was pulled via the distillation system to 30 inches, and the contents were stirred at 185° C. to remove any ethylene glycol by-product formed. The glycol removal was continued at 180°–185° C. for one-half hour. The contents were then cooled, neutralized with phosphoric acid solution (75%) and filtered to yield POE(4) pentaerythritol.

b) Preparation of title compound 526 g (1.7 moles) of the POE(4) pentaerythritol prepared in (a) above was charged to a flask for esterification having standard apparatus for agitation, heating and distillation. Agitation and a dry nitrogen sparge were started, and 1074 g (7.4 moles) of caprylic acid (alkyl chain 98% minimum C8 acid value 388 mg KOH/g) and 0.8 g of hypophosphorous acid solution (50%) were added. The contents were heated to 180° C. with the removal of the water of esterification by distillation and held at 180°–190° C. until all water was removed. The hydroxyl number of the contents was checked, and the reaction was continued at 180°–190° C. until a maximum hydroxyl number of 5.0 mg KOH/g was reached, indicating greater than 99% conversion to the ester. A vacuum was pulled via the distillation system to 30 inches and the contents were stirred at 190° C. to remove the unreacted caprylic acid by distillation. The Acid value of the contents was checked, and the acid removal was continued at 180°–190° C. until a maximum acid value of 1.0 mg KOH/g was reached. The contents were then cooled to 70° C. and filtered to yield a compound of the formula $[C_7H_{15}COO(C_2H_4O)CH_2]_4$-C

EXAMPLE IV

PREPARATION OF POE(4) PENTAERYTHRITOL TETRALAURATE

Following essentially the procedure for Example III, and using in place of caprylic acid an equivalent amount of lauric add (alkyl chain 98% minimum C12, acid value 279 mg KOH/g), a compound of the formula

[C$_{11}$H$_{23}$COO(C$_2$H$_4$O)CH$_2$]$_4$-C was obtained.

EXAMPLE V

PREPARATION OF POE(20) PENTAERYTHRITOL TETRACAPRYLATE a) Preparation of POE(20) Pentaerythritol To a reaction vessel meeting all safety standards for alkoxylation reactions was added 1075 g (3.45 moles) of the POE(4) pentaerythritol prepared in Example III(a). Agitation was started, 1.0 g potassium hydroxide (82% minimum purity ground solid) was added, and the reactor was sealed and tested to assure no leakage was present under vacuum or 40 psig pressure. All air was removed from the reactor through a series of four cycles of pulling vacuum to 28 inches of mercury and purging with dry nitrogen to 40 psig. Vacuum was pulled to 28 inches of mercury and the reactor contents were heated to 110° C. The contents were dried under full vacuum at 110°–115° C. until the moisture level was below 0.08%. The reactor was purged to 5 psig with dry nitrogen, and the contents were heated to 140° C. Reactor cooling was started, and 2425 g (55.11 moles) of ethylene oxide were added at such a rate as to maintain the contents at 140°–150° C. for 40 psig pressure. The contents were then held at 150° C. for one hour after the reactor pressure equilibrated to assure all ethylene oxide had reacted, and then vacuum was carefully pulled to 28 inches of mercury. Any traces of unreacted ethylene oxide, were removed under full vacuum at 150° C. for one-half hour, and the contents were cooled to 70° C., neutralized with phosphoric acid solution (75%) and filtered to yield POE(20) pentaerythritol.

b) Preparation of title compound 879 g (0.87 moles) of the POE(20) pentaerythritol prepared in (a) above was charged to a flask for esterification having standard apparatus for agitation, heating and distillation. Agitation and a dry nitrogen sparge were started, and 551 g (3.8 moles) of caprylic acid (alkyl chain 98% minimum C8 acid value 388 mg KOH/g) and 0.8 g of hypophosphorous acid solution (50%) were added. The contents were heated to 180° C. with the removal of the water of esterification by distillation and held at 180°–190° C. until all water was removed. The hydroxyl number of the contents was checked, and the reaction was continued at 180°–190° C. until a maximum hydroxyl number of 5.0 mg KOH/g was reached, indicating greater than 99% conversion to the ester. A vacuum was pulled via the distillation system to 30 inches and the contents were stirred at 190° C. to remove the unreacted caprylic acid by distillation. The Acid value of the contents was checked, and the acid removal was continued at 180°–190° C. until a maximum acid value of 1.0 mg KOH/g was reached. The contents were then cooled to 70° C. and filtered to yield a compound of the formula

[C$_7$H$_{15}$COO(C$_2$H$_4$O)$_5$CH$_2$]$_4$-C

EXAMPLE VI

PREPARATION OF POE(20) PENTAERYTHRITOL TETRALAURATE

Following essentially the procedure for Example V, and using in place of the caprylic acid an equivalent amount of lauric acid (alkyl chain 98% minimum C12, acid value 279 mg KOH/g), a compound of the formula

[C$_{11}$H$_{23}$COO(C$_2$H$_4$O)$_5$CH$_2$]$_4$-C was observed.

EXAMPLE VII

PREPARATION OF PENTAERYTHRITOL TETRAESTER WITH POE(5) CAPRYL ALCOHOL ETHER CARBOXYLIC ACID (a) Preparation of POE(5) capryl alcohol ether carboxylic acid To a reaction vessel was added, with stirring, 10500 g (30 mole) of the 5 mole ethylate of capryl alcohol (alkyl chain 95% minimum C8, hydroxyl number 160 mg KOH/g). The reaction vessel was sealed and degassed four times at approximately 25°–40° C. by alternately pulling 30 inches of vacuum and purging with dry nitrogen. The moisture content of the reaction vessel was checked with preferred percentage of moisture being less than 0.01% of the reaction vessel contents. If the moisture was above 0.01%, the contents of the reaction vessel were dried for 1 hour at 110° C. while pulling 30 inches of vacuum. The system was purged with dry nitrogen to break the vacuum and cooled. Sodium borohydride, 12.6 g, was added to the reaction vessel and the reaction mixture was stirred at 50°–60° C. for one hour. The contents were cooled to 40°–60° C. and 3595 g (32.1 moles) of potassium tert-butoxide was added in two equal parts, waiting 15 minutes between each part. Sodium monochloroacetate. 3670 g (31.5. moles), was added to the reaction vessel with stirring at such a rate that the exotherm could be controlled to maintain the temperature at 50°–75° C. Upon completion of the addition, the temperature of the reaction mixture was maintained at 70°–75 ° C. for 30 minutes, after which time the temperature was raise to 80°–90° C.; and the reaction mixture was stirred for 12 hours at this temperature. The contents were then sampled in the following manner to determine acid value and hydroxyl number as a measure of the extent of reaction. A 40.0 g sample was charged to a vessel and heated to 75°–80° C. with stirring. Then 40.0 g of a hot (75° C.) 7.5% aqueous solution of sulfuric acid was added and the mixture was stirred at 75° C. for one minute. The mixture was transferred to a separatory funnel and the layers allowed to separate. The bottom aqueous layer was discarded and the organic layer was washed twice with 20.0 g each of a hot (75° C.) 10%. aqueous solution of sodium chloride. The organic layer was then isolated and dried in a rotary evaporator at 90°–100° C. The acid value and hydroxyl number of the resulting oil were measured and found to be 126 mg KOH/g and 10 mg KOH/g respectively. A minimum acid value of 125 mg KOH/g and a maximum hydroxyl number of 16 mg KOH/g are preferred which represent a minimum 90% conversion of the alcohol ethoxylate into the ether carboxylic acid. If the acid value is low and the hydroxyl number is high, the contents of the reaction vessel may be stirred an additional 6 hours at 80°–90° C. and reanalyzed. If the acid value is still low with a high hydroxyl number, it may be necessary to cool the reaction mixture to 40°–50° C. and add additional potassium tert-butoxide equivalent to the remaining unreacted alcohol ethoxylate. After stirring 15 minutes at 40°–50° C., heat the contents to 60°–70° C. and add an equivalent amount of sodium monochloroacetate. Stir the reaction mixture at 70°–90° C. for 4 hours and re-check the acid value and hydroxyl number as before. When the values for the acid value and hydroxyl number were acceptable, vacuum was slowly pulled on the reaction vessel to 30 inches, being careful to avoid foaming, and the reaction mixture was stirred at 70°–90° C. under 30 inches of vacuum for 30 minutes to remove the tert-butyl alcohol. The vacuum was broken with nitrogen, and 17800 g of a 7.5% aqueous solution of sulfuric acid which had been heated to 80° C. was added slowly while maintaining the temperature at 70°–80° C. The resulting mixture was stirred for one minute and transferred to a separator), funnel where the layers were allowed to separate. The bottom aqueous layer was discarded, and the organic layer was washed twice with 9000 g of hot (80° C.) 10% aqueous solution of sodium chloride. The organic layer was then isolated and dried. The resulting oil was filtered to yield a compound of the formula

$C_8H_{17}\text{-O-}(C_2H_4O)_5\text{-}CH_2COOH$ (b) Preparation of title compound 10200 g (25 moles) of the compound prepared in (a) above was charged to a flask for esterification having standard apparatus for agitation heating and distillation. Agitation and a dry nitrogen sparge were started, and 788 g (5.8 moles) of pentaerythritol and 6.6 g of hypophosphorous acid solution (50%) were added. The contents were heated to 190° C. with the removal of water by distillation and held at 190°–195° C. until all water was removed. The acid value of the contents was checked, and the reaction was continued at 190°–195° C. until a maximum acid value of 2.0 mg KOH/g was reached, indicating approximately 99% conversion to the ester. The contents were then cooled to 70° C. and filtered to yield a compound of the formula

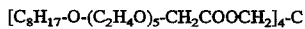

$[C_8H_{17}\text{-O-}(C_2H_4O)_5\text{-}CH_2COOCH_2]_4\text{-C}$

EXAMPLE VIII

Following essentially the procedure of Example VII and using an equivalent amount of the appropriate starting ethoxylate, the following compounds were obtained:

a) Pentaerythritol tetraester with POE(1) capryl alcohol ether carboxylic acid starting with the one mole ethoxylate of capryl alcohol (alkyl chain 95% minimum $C_8$, hydroxyl number 322 mg KOH/g).

b) Pentaerythritol tetraester with POE(1) lauryl alcohol ether carboxylic acid starting with the one mole ethocylate of lauryl alcohol (alkyl chain 95% minimum C12, hydroxyl number 244 mg KOH/g).

c) Pentaerythritol tetraester with POE(5) lauryl alcohol ether carboxylic acid starting with the 5 mole ethoxylate of lauryl alcohol (alkyl chain 95% minimum C12, hydroxyl number 138 mg KOH/g).

d) Pentaerythritol tetraester with POE(5) capryl mercaptan ether carboxylic acid starting with the 5 mole ethoxylate of capryl mercaptan (alkyl chain 95% minimum C8, hydroxyl number 153 mg KOH/g).

e) Pentaerythritol tetraester with POE(5) lauryl mercaptan ether carboxylic acid starting with the 5 mole ethoxylate of lauryl mercaptan (alkyl chain 95% minimum C12, hydroxyl number 133 mg KOH/g).

TEST RESULTS

Comparisons were made of physical properties, thermal stabilities and fiber-to-metal and fiber-to-fiber frictions of various existing polyol fatty acid esters and fatty acid esters of ethoxylated polyols and the corresponding ether carboxylic acid esters of polyols described hereinabove. Viscosity was measured in centipoise at 25° C. using a Brookfield Model LVT viscometer and spindle number 2 at 60 RPM. Dispersibility was measured at 25° C. with 1 weight percent compound in water. Thermal stability was measured on a thermogravimetric analyzer under air comparing the percent weight loss registered at 365° C. on the compound itself and the compound mixed with 0.5% Irganox 1010 antioxidant. Frictions were measured in grams using a Rothschild F meter model R-1188 with a number 1 polished chrome pin and fiber speeds of 100 meters per minute, 50 meters per minute and 0.5 centimeter per minute. Contact angles of 180° for fiber-to-metal friction and 1080° for fiber-to-fiber friction were used. Stickslip was calculated as the difference between the average maximum and the average minimum readings of the fiber-to-fiber friction at 0.5 centimeter per minute fiber speed. The compound to be tested was applied at 1.0 weight percent on the weight of fiber to 40/13 denier textured nylon 6,6, and the fiber was conditioned at 71° F. and 48.8% relative humidity for 24 hours before testing.

As can be readily seen from the data in Table 1, liquidity and dispersibility can be imparted to polyesters by making them with ether carboxylic acids as well as by ethoxylating the polyol before esterification with a fatty acid. The data in Table 2 readily shows, however, that the polyol esters made from ether carboxylic acids as described hereinabove have much better thermal stability than fatty acid esters of ethoxylated polyols. The data in Table 3 readily shows that the more thermally stable ether carboxylic acid polyol esters as described hereinabove are comparable lubricants for synthetic fibers as the known, less thermally stable fatty acid esters of ethoxylated polyols. This data indicates that the present compounds have desirable thermal stability and hydrophilicity and impart desirable lubricity onto commercially important fibers.

TABLE 1

PHYSICAL PROPERTIES

| PRODUCT | Viscosity 25° C., CPS | Dispersibility 1% in water |
|---|---|---|
| Example 1 | 50 | insoluble |
| Example III | 55 | insoluble |
| Example VIIIa | 150 | insoluble |
| Example V | 135 | dispersible |
| Example VII | 210 | dispersible |
| Example VIIId | 125 | dispersible |
| Example II | solid | insoluble |
| Example IV | 95 | insoluble |
| Example VIIIb | 210 | insoluble |
| Example VI | 165 | dispersible |
| Example VIIIc | 285 | dispersible |
| Example VIIIe | 220 | dispersible |

TABLE 2

THERMAL STABILITY
TGA percent weight loss at 365° C.

| PRODUCT | as is | with antioxidant |
|---|---|---|
| Example 1 | 72.5 | 83.2 |
| Example III | 86.0 | 88.5 |
| Example VIIIa | 81.5 | 79.1 |
| Example V | 92.0 | 92.4 |
| Example VII | 74.0 | 81.8 |
| Example VIIId | 55.0 | 58.5 |
| Example II | 28.0 | 39.9 |
| Example IV | 74.0 | 82.0 |
| Example VIIIb | 65.0 | 64.2 |

TABLE 2-continued

THERMAL STABILITY
TGA percent weight loss at 365° C.

| PRODUCT | as is | with antioxidant |
|---|---|---|
| Example VI | 92.0 | 91.6 |
| Example VIIIc | 85.0 | 84.6 |
| Example VIIIe | 20.5 | 55.6 |

TABLE 3

FIBER LUBRICITY

| PRODUCT | F/M [g] 100 m/min | F/F [g] 50 m/min | F/F (S-S) [g] 0.5 cm/min |
|---|---|---|---|
| Example I | 23.2 | 13.2 | 12.2 (1.6) |
| Example III | 23.9 | 13.8 | 11.6 (2.0) |
| Example VIIIa | 34.1 | 14.2 | 12.3 (2.3) |
| Example V | 40.2 | 15.0 | 12.4 (2.1) |
| Example VII | 45.8 | 14.9 | 11.0 (2.1) |
| Example VIIId | 40.8 | 14.9 | 10.9 (0.9) |
| Example II | 15.8 | 12.4 | 11.4 (1.5) |
| Example IV | 28.8 | 13.1 | 12.9 (1.8) |
| Example VIIIb | 33.3 | 13.6 | 10.6 (2.0) |
| Example VI | 33.1 | 13.4 | 13.1 (2.5) |
| Example VIIIc | 48.0 | 15.5 | 11.4 (1.6) |
| Example VIIIe | 38.0 | 16.5 | 10.2 (0.5) |

Other examples of the invention that were produced included: 1) X is oxygen, n is 1, m is 8, p is 4 and R is about 45% $C_8$-alkyl and about 55% $C_{10}$-alkyl; 2) X is oxygen, n is 1, m is 8, p is 3, q is 1, R is about 45% $C_8$-alkyl and about 55% $C_{10}$-alkyl and $R^1$ is $C_2$-alkyl and 3) X is oxygen, n is 1, m is 8, p is 2, q is 1, r is 1, R is about 45% $C_8$-alkyl and about 55% $C_{10}$-alkyl and $R^1$ and $R^2$ are $C_1$-alkyls.

While there is shown and described herein certain specific structure embodying the invention, it will be manifest to those skilled in the art that various modifications and rearrangements of the parts maybe made without departing from the spirit and scope of the underlying inventive concept and that the same is not limited to the particular forms herein shown and described.

What is claimed is:

1. A method for imparting lubricity in a fiber which comprises applying to said fiber an effective lubricating amount of a compound of the general formula (I)

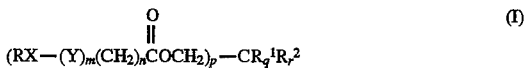

wherein R is alkyl from about 4 to about 22 carbon atoms, $R^1$ and $R^2$ independently of one another, are alkyl from about 1 to about 22 carbon atoms, X is either sulphur or oxygen, Y is $-C_2H_4O-$ or $-C_3H_6O-$ or a mixture of $-C_2H_4O$ and $-C_3H_6O-$, m is a number from about 1 to about 20, n is a number from about 1 to about 6, p is a number from 2 to 4, q is a number from 0 to about 2 and r is a number from 0 to about 2, with q+r+p being the integer 4.

2. The method as claimed in claim 1, wherein X is oxygen and n is a number from about 1 to about 4.

3. The method as claimed in claim 2, wherein n is 1 and m is 8.

4. The method as claimed in claim 1, wherein R is about 45% $C_8$-alkyl and about 55% $C_{10}$-alkyl.

5. The method as claimed in claim 1, wherein p is 4, q is 0 and r is 0.

6. The method as claimed in claim 5 wherein n is 1 and X is oxygen.

7. The method as claimed in claim 6, wherein R is $C_8$ or $C_{12}$ alkyl and m is 1.

8. The method as claimed in claim 6, wherein m is 5; and R is either $C_8$ or $C_{12}$ alkyl.

9. The method as claimed in claim 5, wherein m is 5, n is 1, X is S; and R is $C_8$ or $C_{12}$ alkyl.

10. The method as claimed in claim 1, wherein p is 3, q is 1 and $R^1$ is a $C_2$-alkyl.

11. The method as claimed in claim 1, wherein p is 2, q is 1, r is 1 and $R^1$ and $R^2$ are $C_1$-alkyls.

* * * * *